US010245617B2

(12) United States Patent
Habraken et al.

(10) Patent No.: US 10,245,617 B2
(45) Date of Patent: Apr. 2, 2019

(54) SYNTHESIS OF SURFACE-FUNCTIONALIZED POLYAMIDES

(71) Applicant: BASF SE, Ludwigshafen (DE)

(72) Inventors: Gijsbrecht Jacobus Maria Habraken, Ludwigshafen (DE); Johannes Klaus Sprafke, Speyer (DE); Marion da Silva, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/741,300

(22) PCT Filed: Jul. 6, 2016

(86) PCT No.: PCT/EP2016/066008
§ 371 (c)(1),
(2) Date: Jan. 2, 2018

(87) PCT Pub. No.: WO2017/005804
PCT Pub. Date: Jan. 12, 2017

(65) Prior Publication Data
US 2018/0186956 A1     Jul. 5, 2018

(30) Foreign Application Priority Data
Jul. 9, 2015   (EP) ...................................... 15176129

(51) Int. Cl.
*B05D 1/36* (2006.01)
*B05D 3/00* (2006.01)
*B05D 3/10* (2006.01)
*B05D 7/00* (2006.01)
*B05D 7/02* (2006.01)
*C08J 7/12* (2006.01)
*C07B 37/12* (2006.01)
*C08G 69/48* (2006.01)
*C08L 77/06* (2006.01)

(52) U.S. Cl.
CPC ............... *B05D 3/107* (2013.01); *B05D 1/36* (2013.01); *B05D 3/007* (2013.01); *B05D 3/10* (2013.01); *B05D 3/105* (2013.01); *B05D 7/02* (2013.01); *B05D 7/50* (2013.01); *C07B 37/12* (2013.01); *C08G 69/48* (2013.01); *C08J 7/12* (2013.01); *C08L 77/06* (2013.01); *B05D 2201/02* (2013.01); *B05D 2505/00* (2013.01); *C08J 2377/00* (2013.01); *C08J 2377/06* (2013.01); *C08J 2453/00* (2013.01)

(58) Field of Classification Search
CPC . B05D 1/36; B05D 3/007; B05D 3/10; B05D 3/105; B05D 3/107; B05D 7/02; B05D 7/04; B05D 7/50; B05D 2201/02; B05D 2505/00; C07B 37/12; C08J 7/12; C08J 2377/00; C08J 2453/00
USPC ........................................ 427/337; 428/474.4
See application file for complete search history.

(56) References Cited

U.S. PATENT DOCUMENTS

| 2010/0297556 A1* | 11/2010 | Cameron | C08F 220/36 430/271.1 |
| 2011/0003250 A1* | 1/2011 | Amara | C08F 220/36 430/271.1 |
| 2014/0135449 A1* | 5/2014 | Jeol | C08G 69/26 524/606 |

OTHER PUBLICATIONS

Gousse et al., "Application of the Diels-Alder Reaction to Polymers Bearing Furan Moieties. 2. Diels-Alder and Retro-Diels-Alder Reactions Involving Furan Rings in Some Styrene Copolymers," Macromolecules, vol. 31, No. 2, 1998, pp. 314-321. (Year: 1998).*
Moreno-Couranjou et al., "A Novel Dry Chemical Path Way for Diene and Dienophile Surface Functionalization toward Thermally Responsive Metal-Polymer Adhesion," ACS Appl. Mater. Interfaces 2013, 5, 8446-8456. (Year: 2013).*
Mitiakoudis, A., et al., "Synthesis and Characterization of Furanic polyamides," *Macromolecules* 24, No. 4 (1991), pp. 830-835.
Moreau, C., et al., "Recent Catalytic Advances in the Chemistry of Substituted Furans From Carbohydrates and in the Ensuing Polymers," *Topics in Catalysis* 27, No. 1-4 (2004), pp. 11-30.
International Preliminary Report on Patentability in corresponding international application No. PCT/EP2016/066008, dated Sep. 13, 2016 (English translation).
International Search Report for PCT Patent Application No. PCT/EP2016/066008, dated Sep. 13, 2016 (English translation).
International Patent Application No. PCT/EP2014/077565, filed Dec. 12, 2014.
International Patent Application No. PCT/EP2015/069164, filed Aug. 20, 2015.
U.S. Appl. No. 14/911,561, filed Feb. 11, 2016.
U.S. Appl. No. 14/913,114, filed Feb. 19, 2016.
U.S. Appl. No. 14/913,223, filed Feb. 19, 2016.
U.S. Appl. No. 14/913,119, filed Feb. 19, 2016.
International Patent Application No. PCT/EP2016/066032, filed Jul. 6, 2016.
International Patent Application No. PCT/EP2016/066029, filed Jul. 6, 2016.
U.S. Appl. No. 15/103,483, filed Jun. 10, 2016.
U.S. Appl. No. 15/102,947, filed Jul. 25, 2016.
U.S. Appl. No. 15/103,468, filed Aug. 16, 2016.
U.S. Appl. No. 15/519,850, filed Apr. 18, 2017.

* cited by examiner

*Primary Examiner* — William P Fletcher, III
(74) *Attorney, Agent, or Firm* — Marshall, Gerstein & Borun LLP

(57) ABSTRACT

The present invention relates to a process for producing a surface-functionalized molding (oF) having a functionalized surface (fO). In this process a surface (O) of a molding (F) is brought into contact with a dienophile-containing solution (dL). The surface (O) comprises a polyamide (P) which comprises furan units. These furan units are able to react with the at least one dienophile present in the dienophile-containing solution (dL) to give the surface-functionalized molding (oF) having the functionalized surface (fO).

14 Claims, No Drawings

SYNTHESIS OF SURFACE-FUNCTIONALIZED POLYAMIDES

CROSS-REFERENCE TO RELATED APPLICATIONS

This application is the U.S. National Phase of PCT/EP2016/066008, filed Jul. 6, 2016, which claims the benefit of European Patent Application No. 15176129.3, filed on Jul. 9, 2015.

The present invention relates to a process for producing a surface-functionalized molding (oF) having a functionalized surface (fO). In this process a surface (O) of a molding (F) is brought into contact with a dienophile-containing solution (dL). The surface (O) comprises a polyamide (P) which comprises furan units. These furan units are able to react with the at least one dienophile present in the dienophile-containing solution (dL) to give the surface-functionalized molding (oF) having the functionalized surface (fO).

The present invention further relates to a surface-functionalized molding (oF) obtainable by the process of the invention.

Polyamides in general are semicrystalline polymers which are of particular importance industrially on account of their very good mechanical properties. In particular they possess high strength, stiffness, and toughness, good chemical resistance, and a high abrasion resistance and tracking resistance. These properties are particularly important for the production of injection moldings. High toughness is particularly important for the use of polyamides as packaging films. On account of their mechanical properties, polyamides are used industrially for producing textiles such as fishing lines, climbing ropes, and carpeting. Polyamides also find use for the production of wall plugs, screws, and cable ties. Polyamides, furthermore, are employed as paints, adhesives, and coating materials.

Over the course of recent years, surfaces which repel fluids have become increasingly important, and of particular importance in this context are, in particular, water-repellent (hydrophobic) and oil-repellent (oleophobic; hydrophilic) surfaces. Polyamides frequently do not possess sufficiently liquid-repellent surfaces, and so in certain areas of application it is necessary to use polyamides whose surface has been functionalized to give sufficiently liquid-repellent surfaces. Described in the prior art are a variety of processes for producing more strongly liquid-repellent surfaces on polymers, particularly on polyamides. One possibility involves polymerizing the polyamides, during their preparation, with hydrophobic or hydrophilic comonomers or polymers, to give a copolymer. It is also possible to graft a polyamide with oleophobic or hydrophobic polymers.

With both techniques a disadvantage is that the resulting copolymers or grafted polyamides, respectively, frequently have properties different from those of the pure polyamides. For example, the glass transition temperature $T_G$ may alter, and the crystallinity of the polymers is reduced under certain circumstances. Moreover, the techniques are synthetically complex and entail high costs.

A further problem is that moldings fabricated from the copolymers thus produced have not necessarily been modified on their entire surface, and the liquid-repellent properties are obtained only at those locations on the surface where the hydrophobic or oleophobic regions on the surface are located.

Described in the prior art, therefore, are processes with which the surfaces of shaped articles can be given an inherent hydrophobic or oleophobic modification, by being coated, for example, with a hydrophobic or oleophobic polymer film, in order thus to generate liquid-repellent surfaces on the shaped articles. Furthermore, the structure of the surface can be modified at the micrometer or nanometer range, by means of structuring or roughening of the surface, for example. Combinations of the techniques are of course also possible.

A disadvantage with these techniques, however, is the complex construction of apparatus. It is necessary, moreover, to ensure that the hydrophobic or oleophobic polymers which are to be applied as a polymer film to the molding are compatible with the polymers present in the molding, so that the hydrophobic or oleophobic polymer film remains adhering on the molding.

There is therefore a need for processes which allow the production of surface-functionalized moldings which do not have the disadvantages described above, or have then to a reduced extent.

The object on which the present invention is based is therefore that of providing a process for producing a surface-functionalized molding that does not have, or has only to a reduced extent, the above-described disadvantages of the techniques for producing surface-functionalized moldings. The process, moreover, ought to be able to be carried out extremely simply and inexpensively.

This object is achieved by means of a process for producing a surface-functionalized molding (oF) having a functionalized surface (fO), comprising the steps of i) providing a molding (F) having a surface (O) which comprises a polyamide (P), the polyamide (P) comprising diene units of the general formula (I)

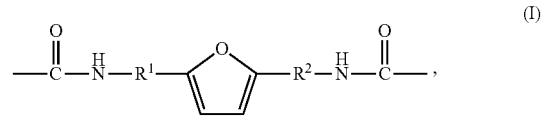

in which

R$^1$ and R$^2$ independently of one another are selected from C$_1$-C$_{10}$ alkanediyl, ii) contacting the surface (O) of the molding (F) provided in step i) with a dienophile-containing solution (dL) which comprises at least one dienophile, the at least one dienophile comprising at least one dienophile unit which is reactive toward the diene units (I) present in the polyamide (P), to give the surface-functionalized molding (oF) having the functionalized surface (fO).

A feature of the process of the invention is its ease of implementation. Through the process of the invention it is possible to carry out targeted modification of the surface (O) of the molding (F). Another advantage is that exclusively the surface (O) of the molding (F) is functionalized. This means that the properties of the material present in the molding (F), particularly of the polymer, such as its mechanical properties, for example, are retained, and that therefore the properties of the molding (F) are retained as well, and only the surface (O) is functionalized. Another advantage is that the functionalization of the surface (O) is reversible and therefore that even later the properties of the functionalized surface (fO) can be modified.

The process of the invention is elucidated in more detail below.

Step i)

Step i) provides a molding (F) having a surface (O) which comprises a polyamide (P), the polyamide (P) comprising diene units (I).

The molding (F) may have any of the forms known to the skilled person. It may be present, for example, in the form of powder, pellets, film, sheet or finished component. Preferably it takes the form of a sheet or a finished component.

"Film" in the context of the present invention refers to a planar molding (F) having a thickness in the range from 20 µm to 500 mm, preferably in the range from 50 µm to 300 µm. "Sheet" refers to a planar molding (F) having a thickness in the range from >0.5 mm to 100 mm.

A powder for the purposes of the present invention means particles having a size in the range from 1 to 500 µm, preferably in the range from 20 to 150 µm, as determined by sieving, light scattering or microscopy.

Pellets for the purposes of the present specification are particles having a size in the range from >0.5 to 10 mm, preferably in the range from 1 to 5 mm, determined by microscopy or a caliper gauge.

Finished components which may be used as molding (F) are, for example, components for the construction sector, automaking, marine construction, rail vehicle construction, container construction, for sanitary installations and/or for aerospace travel. Preferred finished components are, for example, dashboards, packaging films, and monofilaments, for fishing nets or fishing lines, for example.

The molding (F) may comprise any materials known to the skilled person, with the proviso that it has a surface (O) which comprises a polyamide (P) which comprises diene units (I). The molding preferably comprises at least one polymer. More preferably the molding (F) comprises at least one polyamide, especially preferably the polyamide (P) which comprises diene units (I).

For example, the molding comprises at least 20 wt %, preferably at least 50 wt %, and especially preferably at least 90 wt % of the polyamide (P) which comprises diene units (I), based on the total weight of the at least one polymer present in the molding (F), preferably based on the total weight of the molding (F).

For the polyamide (P) optionally present in the molding (F) and comprising diene units (I), the statements and preferences described below for the polyamide (P), that comprises diene units (I) and is present in the surface (O) apply correspondingly.

The molding (F) may further comprise additives. Additives of this kind are known to the skilled person and are, for example, flame retardants, fillers, reinforcing materials, plasticizers, antioxidants, UV stabilizers, and pigments.

Customarily the molding (F) comprises in the range from 0 to 70 wt %, preferably in the range from 0.5 to 50 wt %, and especially preferably in the range from 1 to 35 wt % of the additives based on the total weight of the molding (F).

In accordance with the invention the molding (F) has a surface (O) which comprises the polyamide (P) that comprises diene units (I).

The term "a surface (O)" presently refers to not only exactly one surface but also two or more surfaces.

The surface (O) which comprises the polyamide (P) that comprises diene units (I) may be formed locally at a predetermined position of the molding (F). It is also possible for the surface (O) to fully surround the molding (F). A further possibility is for the molding (F) to have the surface (O) only on the top face of the molding (F) or only on the bottom face of the molding (F).

Where the surface (O) is formed only locally at one position on the molding (F), the surface (O) forms, for example, 1% to 99% of the total surface area of the molding (F), preferably 10% to 60%, and especially preferably 20% to 40% of the total surface area of the molding (F).

In accordance with the invention the surface (O) comprises the polyamide (P) that comprises diene units (I). The surface (O) comprises, for example, in the range from 30 to 100 wt % of the polyamide (P), preferably in the range from 80 to 99 wt % of the polyamide (P), and especially preferably in the range from 95 to 99 wt % of the polyamide (P), based in each case on the total weight of the surface (O).

The surface (O) may further comprise further polymers, different from the at least one polyamide (P). Polymers of this kind are known to the skilled person.

The surface (O) may further comprise additives. Additives of this kind are known to the skilled person and are, for example, flame retardants, reinforcing agents, fillers, plasticizers, antioxidants, UV stabilizers, and pigments.

For example the surface (O) comprises in the range from 0 to 70 wt %, preferably in the range from 1 to 20 wt %, and especially preferably in the range from 1 to 5 wt % of the additives, based on the total weight of the surface (O).

"A polyamide (P)" means in the context of the present invention not only exactly one polyamide (P) but also a mixture of two or more polyamides (P).

The surface (O) comprises the polyamide (P) which comprises the diene units as repeating units of the general formula (I)

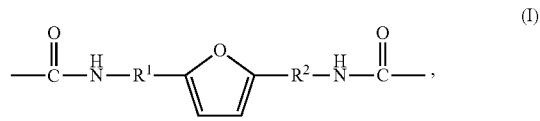

in which $R^1$ and $R^2$ have the definitions described above.

The diene units are also referred to as "furan units". The terms "furan units" and "diene units" are used synonymously in the context of the present invention and therefore possess the same meaning.

The furan units as repeating units of the general formula (I) are present preferably in the main chain of the polyamide (P). Especially preferably the polyamide (P) contains no side chains which comprise furan units as repeating units of the general formula (I), and most preferably the polyamide (P) contains no side chains. The polyamide (P) is therefore most preferably a linear polyamide (P).

In one preferred embodiment $R^1$ and $R^2$ in the general formula (I) have the definitions below.

$R^1$ and $R^2$ are selected independently of one another from $C_1$-$C_4$ alkanediyl,
preferably $R^1$ and $R^2$ are the same $C_1$-$C_4$ alkanediyl, and most preferably in the general formula (I)
$R^1$ and $R^2$ are both methylene.

"$C_1$-$C_{10}$ alkanediyl" as described for example above for $R^1$ and $R^2$ for the diene units of the general formula (I) present in the polyamide (P) means in the context of the present invention a hydrocarbon having 1 to 10 carbon atoms and two free valences. It is therefore a biradical having 1 to 10 carbon atoms. "$C_1$-$C_{10}$ alkanediyl" encompasses both linear and cyclic, and also saturated and unsaturated, hydrocarbons having 1 to 10 carbon atoms and two free valences. Hydrocarbons having a cyclic fraction and a linear fraction are likewise included by the term "$C_1$-$C_{10}$ alkanediyl". Examples of $C_1$-$C_{10}$ alkanediyls are methylene, ethylene (ethane-1,2-diyl, dimethylene), propane-1,3-diyl (trimethylene), propylene (propane-1,2-diyl), and butane-1,4-diyl (tetramethylene). Corresponding observations apply in respect of "$C_1$-$C_4$ alkanediyl".

The polyamide (P) may be prepared by any methods known to the skilled person.

In one preferred embodiment the polyamide (P) is prepared by polymerization from a reaction mixture (RM) at a reaction temperature $T_R$, the reaction mixture (RM) comprising the components below.

A1) at least one lactam
A2) at least one diamine of the general formula (II)

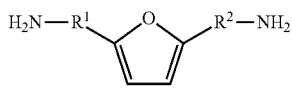
(II)

in which
$R^1$ and $R^2$ independently of one another are selected from $C_1$-$C_{10}$ alkanediyl, A3) at least one dicarboxylic acid derivative selected from the group consisting of a dicarboxylic acid of the general formula (III), a dicarboxylic ester of the general formula (IV), and a dinitrile of the general formula (V)

  (III)

  (IV)

  (V)

in which
$R^3$, $R^4$ and $R^7$ independently of one another are selected from the group consisting of a bond, unsubstituted or at least monosubstituted $C_1$-$C_{40}$ alkanediyl, and unsubstituted or at least monosubstituted $C_6$-$C_{40}$ arylene, where the substituents are selected from the group consisting of F, Cl, Br, I, $OR^8$, $C_1$-$C_{10}$ alkyl, and $C_6$-$C_{10}$ aryl, where
$R^8$ is selected from the group consisting of H and $C_1$-$C_{10}$ alkyl;
$R^5$ and $R^6$ independently of one another are selected from the group consisting of unsubstituted or at least monosubstituted $C_1$-$C_{20}$ alkyl, unsubstituted or at least monosubstituted $C_6$-$C_{20}$ aryl, and unsubstituted or at least monosubstituted $C_6$-$C_{20}$ aralkyl, where
the substituents are selected from the group consisting of F, Cl, Br, I, $OR^9$, and $C_1$-$C_{10}$ alkyl, where
$R^9$ is selected from the group consisting of H and $C_1$-$C_{10}$ alkyl; and A4) water.

The reaction mixture (RM) comprises as component A1) at least one lactam, as component A2) at least one diamine (II), as component A3) at least one dicarboxylic acid derivative, selected from the group consisting of a dicarboxylic acid (III), a dicarboxylic ester (IV), and a dinitrile (V), as component A4) water, and optionally, as component A5), from 0 to 5 wt % of at least one endgroup regulator, based on the total weight of components A1) to A5).

In one embodiment of the present invention the reaction mixture (RM) comprises as component A1) in the range from 26 to 98 wt % of at least one lactam, as component A2) in the range from 0.5 to 35 wt % of at least one diamine (II), as component A3) in the range from 0.5 to 30 wt % of at least one dicarboxylic acid derivative, as component A4) in the range from 1 to 30 wt % of water, and as component A5) in the range from 0 to 1 wt % of at least one endgroup regulator, the weight percentages being based in each case on the total weight of components A1) to A4) or based on the total weight of components A1) to A5) in the event that the reaction mixture (RM) includes the component A5).

In accordance with the invention the wt % figures of components A1), A2), A3), A4) and, optionally, of component A5) are based on the total weight of the components A1), A2), A3), A4) and, optionally, component A5) present in the reaction mixture (RM).

Where component A5) is not included in the reaction mixture (RM), the wt % figures of components A1), A2), A3), and A4) are based on the total weight of the components A1), A2), A3), and A4) present in the reaction mixture (RM).

In the event that component A5) is included in the reaction mixture (RM), the wt % figures of components A1), A2), A3), A4), and A5) are based on the total weight of the components A1), A2), A3), A4), and A5) present in the reaction mixture (RM).

In one preferred embodiment the wt % figures of components A1), A2), A3), A4) and, optionally, of component A5) are based on the total weight of the reaction mixture (RM).

In one embodiment of the present invention the reaction mixture (RM) therefore comprises
26 to 98 wt % of component A1),
0.5 to 35 wt % of component A2),
0.5 to 30 wt % of component A3), and
1 to 30 wt % of component A4),
the weight percentages being based in each case on the total weight of components A1) to A4) or based on the total weight of components A1) to A5), preferably based on the total weight of the reaction mixture (RM).

In one preferred embodiment of the present invention the reaction mixture (RM) comprises
50 to 89 wt % of component A1),
5 to 25 wt % of component A2),
5 to 25 wt % of component A3),
1 to 20 wt % of component A4), and
0.1 to 0.9 wt % of component A5),
the weight percentages being based in each case on the total weight of components A1) to A5), preferably based on the total weight of the reaction mixture (RM).

In one particularly preferred embodiment of the present invention the reaction mixture (RM) therefore comprises
75 to 82 wt % of component A1),
8 to 12 wt % of component A2),
8 to 13 wt % of component A3),
1 to 5 wt % of component A4), and
0.1 to 0.75 wt % of component A5),
the weight percentages being based in each case on the total weight of components A1) to A5), preferably based on the total weight of the reaction mixture (RM).

The sum of the weight percentages of the components A1) to A5) adds up in general to 100 wt %.

Unless otherwise indicated, all of the weight percent figures of the components A1) to A5) are based on the composition of the reaction mixture (RM) before the beginning of the polymerization. The phrase "composition of the reaction mixture (RM) before the beginning of the polymerization" refers in the context of the present invention to the composition of the reaction mixture (RM) before the components A1) to A5) present in the reaction mixture (RM) begin to react with one another, in other words before the polymerization sets in. The components A1) to A5) present in the reaction mixture (RM) are at that point therefore still in their unreacted form. It is self-evident that during the polymerization the components A1) to A5) present in the reaction mixture (RM) react at least partly with one another and therefore that the proportion of the components A1) to A5) among one another changes, just as the components A1) to A5) present in the reaction mixture (RM) change during the polymerization. The skilled person is aware of these reactions.

Lactam in accordance with the invention refers to cyclic amides which have 3 to 12 carbon atoms in the ring, preferably 6 to 12 carbon atoms. Suitable lactams are for example selected from the group consisting of 3-aminopropanolactam (β-lactam; β-propiolactam), 4-aminobutanolactam (γ-lactam; γ-butyrolactam), 5-aminopentanolactam (δ-lactam; δ-valerolactam), 6-aminohexanolactam (ε-lactam; ε-caprolactam), 7-aminoheptanolactam (ζ-lactam; ζ-heptanolactam), 8-aminooctanolactam (η-lactam; η-octanolactam), 9-nonanolactam (θ-lactam; θ-nonanolactam), 10-decanolactam (ω-decanolactam), 11-undecanolactam (ω-undecanolactam), and 12-dodecanolactam (ω-dodecanolactam).

The lactams may be unsubstituted or at least monosubstituted. Where at least monosubstituted lactams are used, they may carry, on the carbon atoms of the ring, one, two or more substituents which are selected independently of one another from the group consisting of $C_1$ to $C_{10}$ alkyl, $C_5$ to $C_6$ cycloalkyl, and $C_5$ to $C_{10}$ aryl.

Suitability as $C_1$ to $C_{10}$ alkyl substituents is possessed for example by methyl, ethyl, propyl, isopropyl, n-butyl, sec-butyl, and tert-butyl. An example of a suitable $C_5$ to $C_6$ cycloalkyl substituent is cyclohexyl. Preferred $C_5$ to $C_{10}$ aryl substituents are phenyl and anthranyl.

Preference is given to using unsubstituted lactams, in which case 12-dodecanolactam (ω-dodecanolactam) and ε-lactam (ε-caprolactam) are preferred. Particularly preferred is ε-lactam (ε-caprolactam).

ε-Caprolactam is the cyclic amide of caproic acid. It is also referred to as 6-aminohexanolactam, 6-hexanolactam or caprolactam. Its IUPAC name is "acepan-2-one". Caprolactam possesses the CAS number 105-60-2 and the general formula $C_6H_{11}NO$. Processes for preparing caprolactam are known per se to the skilled person.

In one preferred embodiment component A2) is at least one diamine (II) in which $R^1$ and $R^2$ are selected independently of one another from $C_1$-$C_4$ alkanediyl.

More preferably component A2) is at least one diamine (II) in which $R^1$ and $R^2$ are the same $C_1$-$C_4$ alkanediyl.

Especially preferably component A2) is at least one diamine (II) in which $R^1$ and $R^2$ are both methylene.

If $R^1$ and $R^2$ are both methylene, the diamine (II) is 2,5-bis(aminomethyl)furan. 2,5-Bis(aminomethyl)furan has the CAS number 2213-51-6.

In one embodiment, moreover, the reaction mixture (RM) may further comprise at least one further diamine (component A2')).

Suitable further diamines (component A2')) are known per se to the skilled person. It is self-evident that the at least one further diamine (component A2')) is different from component A2), the diamine (II). The at least one further diamine is preferably selected from alkanediamines having 4 to 36 carbon atoms, more particularly alkanediamines having 6 to 12 carbon atoms, and also aromatic diamines. With particular preference the at least one further diamine is selected from the group consisting of 1,4-butanediamine, 1,5-pentanediamine, 1,6-hexamethylenediamine, 1,7-heptamethylenediamine, 1,8-octamethylenediamine, 1,9-nonanediamine, 1,10-decanediamine, 1,11-undecanediamine, 1,12-dodecanediamine, 1,13-tridecanediamine, 1,14-tetradecanediamine, 1,15-pentadecanediamine, 1,16-hexadecanediamine, 1,17-heptadecanediamine, 1,18-octadecanediamine, C36 dimer diamine, bis(4-amino-3-methylcyclohexyl)methane (MACM), 4,4-methylenebis(cyclohexylamine) (PACM), bis(4-amino-3-ethylcyclohexyl)methane (EACM), bis(4-amino-3,5-dimethylcyclohexyl)methane (TMACM), isophoronediamine, m-xylylenediamine, p-xylylenediamine, 2,5-bis(methylamino)tetrahydrofuran, 2,2-di(4-aminophenyl)propane, 2,2-di(4-aminocyclohexyl)propane, 2,4,4-trimethylhexamethylenediamine, and 1,5-diamino-2-methylpentane.

In one preferred embodiment the substituents of component A3) in the formula (III), the formula (IV), and the formula (V) have the following definitions:

$R^3$, $R^4$ and $R^7$ are selected independently of one another from the group consisting of a bond, unsubstituted $C_1$-$C_{36}$ alkanediyl, and $C_6$-$C_{20}$ arylene;

$R^5$ and $R^6$ are selected independently of one another from the group consisting of unsubstituted $C_1$-$C_{10}$ alkyl, $C_6$-$C_{10}$ aryl, and $C_6$-$C_{12}$ aralkyl.

In one especially preferred embodiment the substituents in the formula (III), the formula (IV), and the formula (V) have the following definitions:

$R^3$, $R^4$ and $R^7$ are selected independently of one another from the group consisting of a bond, unsubstituted $C_1$-$C_{12}$ alkanediyl, and $C_6$-$C_{10}$ arylene;

$R^5$ and $R^6$ are selected independently of one another from the group consisting of unsubstituted $C_1$-$C_4$ alkyl, $C_1$-$C_{10}$ aryl, and $C_1$-$C_{12}$ aralkyl.

"$C_1$-$C_{40}$ alkanediyl", as described for $R^3$ in formula (III), for example, is understood in the context of the present invention to refer to a hydrocarbon having two free valences and from 1 to 40 carbon atoms. Expressed otherwise, a $C_1$-$C_{40}$ alkanediyl is a biradical having 1 to 40 carbon atoms. "$C_1$-$C_{40}$ alkanediyl" encompasses both linear and cyclic, and also saturated and unsaturated, hydrocarbons having 1 to 40 carbon atoms and two free valences. Hydrocarbons which have both a linear and a cyclic component are likewise covered by the term. Corresponding statements apply in respect of $C_1$-$C_{36}$ alkanediyl and $C_1$-$C_{12}$ alkanediyl.

"$C_6$-$C_{40}$ arylene" refers to an aromatic hydrocarbon having two free valences and from 6 to 40 carbon atoms. Expressed otherwise, "$C_6$-$C_{40}$ arylene" refers to an aromatic biradical having 6 to 40 carbon atoms. A $C_6$-$C_{40}$ arylene therefore has an aromatic ring system. This ring system may be monocyclic, bicyclic or polycyclic. Corresponding statements apply in respect of $C_6$-$C_{20}$ arylene and $C_6$-$C_{10}$ arylene.

"$C_1$-$C_{20}$ alkyl" refers to saturated and unsaturated hydrocarbons having one free valence (radical) and from 1 to 20 carbon atoms. The hydrocarbons may be linear, branched or cyclic. It is also possible for them to comprise a cyclic component and a linear component. Examples of alkyl groups are methyl, ethyl, n-propyl, isopropyl, n-butyl, isobutyl, sec-butyl, tert-butyl, hexyl, and cyclohexyl. Corresponding statements also apply in respect of $C_1$-$C_{10}$ alkyl.

"$C_6$-$C_{20}$ aryl" denotes the radical of an aromatic hydrocarbon having 6 to 20 carbon atoms. An aryl therefore has an aromatic ring system. This ring system may be monocyclic, bicyclic or polycyclic. Examples of aryl groups are phenyl and naphthyl such as 1-naphthyl and 2-naphthyl, for example.

"$C_6$-$C_{20}$ aralkyl" denotes in the present context that the substituent is an alkyl which in turn is substituted by an aryl. Expressed otherwise, aralkyl describes an alkanediyl which is substituted by an aryl radical. A $C_6$-$C_{20}$ aralkyl is an aralkyl which contains 6 to 20 carbon atoms. The aryl radical may for example be an aryl as defined above. Examples of aralkyl are phenylmethyl (benzyl) or phenylethyl, for example.

In a further preferred embodiment, the at least one dicarboxylic acid derivative (component A3)) is selected from the group consisting of a dicarboxylic acid of the general formula (III) and a dicarboxylic ester of the general formula (IV).

The dicarboxylic acid (III) and the dicarboxylic ester (IV) are then correspondingly subject to the statements and preferences described above.

In another preferred embodiment the dicarboxylic acid (III) is selected from the group consisting of oxalic acid (ethanedioic acid), malonic acid (propanedioic acid), succinic acid (butanedioic acid), glutaric acid (pentanedioic acid), adipic acid (hexanedioic acid), pimelic acid (heptanedioic acid), suberic acid (octanedioic acid), azelaic acid (nonanedioic acid), sebacic acid (decanedioic acid), 1,11-undecanedioic acid, 1,12-dodecanedioic acid, 1,13-tridecanedioic acid, 1,14-tetradecanedioic acid, 1,15-pentadecanedioic acid, 1,16-hexadecanedioic acid, 1,17-heptadecanedioic acid, 1,18-octadecanedioic acid, 1,3-cyclohexanedicarboxylic acid, 1,4-cyclohexanedicarboxylic acid, isophthalic acid, terephthalic acid, naphthalenedicarboxylic acid, C36-dimer acid, 2,5-tetrahydrofurandicarboxylic acid, 2,5-furandicarboxylic acid, monosodium 5-sulfoisophthalate, and monolithium 5-sulfoisophthalate.

In a further, especially preferred embodiment, the dicarboxylic acid (III) is selected from the group consisting of adipic acid (hexanedioic acid), pimelic acid (heptanedioic acid), suberic acid (octanedioic acid), azelaic acid (nonanedioic acid), sebacic acid (decanedioic acid), 1,11-undecanedioic acid, 1,12-dodecanedioic acid, 1,13-tridecanedioic acid, 1,14-tetradecanedioic acid, 1,15-pentadecanedioic acid, 1,16-hexadecanedioic acid, 1,17-heptadecanedioic acid, 1,18-octadecanedioic acid, 2,5-tetrahydrofurandicarboxylic acid, 1,3-cyclohexanedicarboxylic acid, 1,4-cyclohexanedicarboxylic acid, isophthalic acid, terephthalic acid, naphthalenedicarboxylic acid, and C36 dimer acid.

"At least one endgroup regulator" means in the context of the present invention both exactly one endgroup regulator and also a mixture of two or more endgroup regulators.

Endgroup regulators are known per se to the skilled person.

The idea is that the endgroup regulator reacts with the polyamide (P), more particularly with the amine end groups of the polyamide (P), and so transamidation can be prevented.

Examples of suitable endgroup regulators are monocarboxylic acids, monoamines, benzenemonocarboxylic acids, naphthalenemonocarboxylic acids, benzenemonoamines, naphthalenemonoamines, or diacids or anhydrides which form imides with amines.

The at least one endgroup regulator is preferably selected from the group consisting of propionic acid, benzoic acid, naphthoic acid, and succinic anhydride.

The present invention accordingly also provides a process wherein the at least one endgroup regulator is selected from the group consisting of propionic acid, benzoic acid, naphthoic acid, and succinic anhydride.

The polymerization from the reaction mixture (RM) may take place by any methods known to the skilled person. Polymerization takes place preferably at a reaction temperature $T_R$ which is above the melting temperature $T_M$ of the polyamide (P). The reaction temperature $T_R$, for example, is in the range from 190 to 235° C., preferably in the range from 195 to 230° C., and especially preferably in the range from 200 to 220° C.

The polyamide (P) generally has a viscosity number of 30 to 250 ml/g, preferably of 90 to 220 ml/g, and especially preferably in the range from 100 to 130 ml/g. The viscosity number is determined in a solution of 0.5 g of polyamide (P) in 100 ml of a 1:1 mixture of phenol and o-dichlorobenzene.

The weight-average molecular weight ($M_w$) of the polyamide (P) is customarily in the range from 20,000 to 150,000 g/mol, preferably in the range from 30,000 to 140,000 g/mol, and especially preferably in the range from 35,000 to 120,000 g/mol, determined by means of gel permeation chromatography (GPC) (size exclusion chromatography (SEC)). Solvent used was hexafluoroisopropanol (HFIP).

The number-average molecular weight ($M_n$) of the polyamide (P) is customarily in the range from 5000 to 75,000 g/mol, preferably in the range from 15,000 to 70,000 g/mol, and especially preferably in the range from 17,500 to 60,000 g/mol, determined by means of gel permeation chromatography (GPC) (size exclusion chromatography (SEC)). Solvent used was hexafluoroisopropanol (HFIP).

The melting temperature $T_M$ of the polyamide (P) is customarily in the range from 80 to 330° C., preferably in the range from 150 to 250° C., and especially preferably in the range from 180 to 230° C., determined by differential scanning calorimetry (DSC) or by dynamic mechanical thermoanalysis (DMTA) for semicrystalline polyamides. For amorphous polyamides, $T_M$ is defined as the temperature at which the polyamide (P) (having a minimum solution viscosity of 80 mL/g to ISO307 in sulfuric acid) has at least a zero shear viscosity of 5000 Pa s and hence is processable in the melt (measured on a DHR-1 rotational rheometer from TA Instruments, plate/plate geometry, plate diameter 25 mm and sample height 1.0 mm. Deformation 1.0%, preheat time 1.5 min, and material dried under reduced pressure at 80° C. for 7 days beforehand).

The present invention accordingly also provides a process wherein the melting temperature $T_M$ of the polyamide (P) is in the range from 80 to 330° C.

The polyamide (P) customarily has a glass transition temperature $T_G$. The glass transition temperature $T_G$ of the polyamide (P) is customarily in the range from 0 to 150° C., preferably in the range from 20 to 100° C., and especially preferably in the range from 40 to 80° C., determined by DSC.

The present invention accordingly also provides a process wherein the glass transition temperature $T_G$ of the polyamide (P) is in the range from 0 to 150° C.

The molding (F) may be provided in step i) by any methods known to the skilled person. Examples of suitable methods include injection molding, extrusion, calendering, rotomolding, and blow molding; preferred methods are injection molding and/or extrusion.

Step ii)

In step ii) the surface (O) of the molding (F) provided in step i) is brought into contact with a dienophile-containing solution (dL) to give the surface-functionalized molding (oF). The dienophile-containing solution (dL) comprises at least one dienophile. The at least one dienophile comprises at least one dienophile unit which is reactive toward the diene units (I) present in the polyamide (P).

In one preferred embodiment the dienophile-containing solution (dL) comprises at least one solvent (LM). In that case the dienophile-containing solution (dL) comprises, therefore, at least one solvent (LM) and at least one dienophile.

The present invention accordingly also provides a process wherein the dienophile-containing solution (dL) comprises at least one solvent (LM).

In step ii) the entire surface (O) of the molding (F) may be brought into contact with the dienophile-containing solution (dL). This embodiment is preferred. It is possible, furthermore, for only part of the surface (O) of the molding (F) to be brought into contact with the dienophile-containing solution (dL); for example, in the range from 1% to 99% of the surface (O), based on the total surface (O).

The surface (O) may be contacted with the dienophile-containing solution (dL) by any methods known to the skilled person, as for example by immersing at least the surface (O) of the molding (F) into the dienophile-containing solution (dL), or by applying the dienophile-containing solution (dL) to the surface (O) by spraying, rolling, knife coating or brushing. Processes for accomplishing this are known to the skilled person. The surface (O) is preferably brought into contact with the dienophile-containing solution (dL) by immersing at least the surface (O) of the molding (F) into the dienophile-containing solution (dL).

The dienophile-containing solution (dL) comprises for example in the range from 0 to 99.5 wt % of the at least one solvent (LM) and in the range from 0.5 to 100 wt % of the at least one dienophile, based in each case on the sum of the weight percentages of the at least one solvent (LM) and of the at least one dienophile, preferably based on the total weight of the dienophile-containing solution (dL).

Preferably the dienophile-containing solution (dL) comprises in the range from 70 to 98 wt % of the at least one solvent (LM) and in the range from 2 to 30 wt % of the at least one dienophile, based in each case on the sum of the weight percentages of the at least one solvent (LM) and of the at least one dienophile, preferably based on the total weight of the dienophile-containing solution (dL).

More preferably the dienophile-containing solution (dL) comprises in the range from 90 to 97 wt % of the at least one solvent (LM) and in the range from 3 to 10 wt % of the at least one dienophile, based in each case on the sum of the weight percentages of the at least one solvent (LM) and of the at least one dienophile, preferably based on the total weight of the dienophile-containing solution (dL).

The present invention accordingly also provides a process wherein the dienophile-containing solution (dL) comprises in the range from 0 to 99.5 wt % of the at least one solvent (LM) and in the range from 0.5 to 100 wt % of the at least one dienophile, based in each case on the total weight of the dienophile-containing solution (dL).

Suitability as the at least one solvent (LM) preferably present in the dienophile-containing solution (dL) is possessed by all solvents known to the skilled person in which the polyamide (P) present in the surface (O) is insoluble and in which the at least one dienophile is soluble. The at least one solvent (LM) is preferably a nonnucleophilic solvent. Solvents of this kind are known to the skilled person.

Examples of solvents suitable as the at least one solvent (LM) include aprotic-polar solvents, aprotic-apolar solvents, protic solvents, and mixtures thereof.

Examples of suitable aprotic-polar solvents are acetone, acetonitrile, N-methyl-2-pyrrolidone, dimethylformamide, and dimethyl sulfoxide.

Examples of suitable aprotic-apolar solvents include hexane, toluene, diethyl ether, tetrahydrofuran, methylene chloride, chloroform, and 1,2-dichlorobenzene.

Examples of suitable protic solvents are water, methanol, ethanol, and isopropanol.

The at least one solvent (LM) is preferably selected from the group consisting of acetone, acetonitrile, N-methyl-2-pyrrolidone, dimethylformamide, dimethyl sulfoxide, hexane, toluene, diethyl ether, tetrahydrofuran, methylene chloride, chloroform, 1,2-dichlorobenzene, water, methanol, ethanol, and isopropanol. Especially preferably the at least one solvent (LM) is selected from the group consisting of toluene, tetrahydrofuran, water, methanol, ethanol, and isopropanol.

The present invention accordingly also provides a process wherein the at least one solvent (LM) is selected from the group consisting of acetone, acetonitrile, N-methyl-2-pyrrolidone, dimethylformamide, dimethyl sulfoxide, hexane, toluene, diethyl ether, tetrahydrofuran, methylene chloride, chloroform, 1,2-dichlorobenzene, water, methanol, ethanol, and isopropanol.

In accordance with the invention the dienophile-containing solution (dL) comprises at least one dienophile which comprises at least one dienophile unit which is reactive toward the diene units (I) present in the polyamide (P).

"At least one dienophile" means in the context of the present invention not only exactly one dienophile but also a mixture of two or more dienophiles.

"At least one dienophile unit which is reactive toward the diene units (I) present in the polyamide (P)" means that the at least one dienophile may contain exactly one dienophile unit, or else may contain two or more dienophile units. Preferably, in accordance with the invention, the at least one dienophile contains exactly one dienophile unit which is reactive toward the diene units present in the polyamide (P).

The present invention accordingly also provides a process wherein the at least one dienophile present in the dienophile-containing solution (dL) comprises exactly one dienophile unit.

"Dienophile unit which is reactive toward the diene units (I) present in the polyamide (P)" means that the dienophile unit present in the dienophile is able to react with the diene units (I) of the polyamide (P) in a [4+2] cycloaddition. Groups of this kind and the corresponding dienophiles are known per se to the skilled person. The diene unit (I) of the polyamide (P) acts here as a diene component which contributes $4\pi$ electrons to the [4+2] cycloaddition. The dienophile unit of the dienophile contributes $2\pi$ electrons to the [4+2] cycloaddition.

Each diene unit (I) of the polyamide (P) is therefore able to enter into a [4+2] cycloaddition with, respectively, one dienophile unit of the dienophile present in the dienophile-containing solution (dL).

The present invention accordingly also provides a process wherein in step ii) the at least one dienophile unit present in the at least one dienophile reacts with the diene units (I) present in polyamide (P) in a [4+2] cycloaddition to give the surface-functionalized molding (oF).

The at least one dienophile unit present in the dienophile which is reactive toward the diene units (I) (furan units) present in the polyamide (P) is preferably selected from the group consisting of C=C double bonds, C=O double bonds, and C=S double bonds.

The present invention accordingly also provides a process wherein the at least one dienophile unit present in the at least one dienophile is selected from the group consisting of C=C double bonds, C=O double bonds, and C=S double bonds.

In one especially preferred embodiment the at least one dienophile unit present in the dienophile is a C=C double bond.

In a further preferred embodiment, the dienophile comprises at least one dienophile unit which is selected from the group consisting of C=C double bonds, C=O double bonds, and C=S double bonds, the double bonds containing electron-withdrawing substituents.

Electron-withdrawing substituents are known per se to the skilled person. Examples of electron-withdrawing substituents are carboxyl groups, ester groups, amides, nitriles, nitro groups, substituted aryls, fluoroalkyls, and fluorine, for example.

The skilled person is aware that the electron-withdrawing substituents increase the reactivity of the dienophile unit of the dienophile toward the furan units.

In one especially preferred embodiment of the present invention, the at least one dienophile present in the dienophile-containing solution (dL) comprises at least one dienophile unit which is selected from the group consisting of maleimide, benzophenone, acrylates, methacrylates, acrylonitriles, maleic acid, maleic anhydride, and maleic esters.

The present invention accordingly also provides a process wherein the at least one dienophile present in the dienophile-containing solution (dL) comprises at least one structural unit selected from the group consisting of maleimides, benzophenone, acrylates, methacrylates, acrylonitriles, maleic acid, maleic anhydride, and maleic esters.

It is preferred, moreover, for the at least one dienophile to comprise no isocyanate and no carboxylic acid as at least one dienophile unit. Preferably, therefore, the at least one dienophile unit is not an isocyanate and not a carboxylic acid.

The present invention accordingly also provides a process wherein the dienophile unit present in the at least one dienophile is not an isocyanate and not a carboxylic acid.

In one preferred embodiment the at least one dienophile present in the dienophile-containing solution (dL) comprises at least one further functional unit.

"At least one further functional unit" in the context of the present invention means both exactly one further functional unit and also two or more further functional units.

A "functional unit" is taken to be a functional group which is able to enter, with the reactive unit present in the functionalizing agent (FM) described later on below, into a reaction through which the functionalizing agent (FM) is added onto the dienophile.

The present invention accordingly also provides a process wherein the at least one dienophile present in the dienophile-containing solution (dL) comprises at least one further functional unit.

In one embodiment of the present invention the at least one further functional unit is different from the at least one dienophile unit present in the at least one dienophile. This embodiment is preferred.

It is possible, furthermore, for the at least one dienophile unit and the at least one further functional unit to be identical. For example, the at least one dienophile may comprise exactly two dienophile units, with one of the dienophile units reacting with the diene unit (I) present in the polyamide (P), and the second of the dienophile units not reacting with the diene unit (I) present in the polyamide (P). The second of the dienophile units is in that case the further functional unit.

Suitability as at least one further functional unit is possessed by all functional units known to the skilled person.

Preferably the at least one further functional unit which is present in the at least one dienophile is selected from the group consisting of anhydrides, imides, esters, carboxylic acids, amines, alcohols, thiols, and isocyanates.

The present invention accordingly also provides a process wherein the at least one dienophile comprises as at least one further functional unit a functional unit selected from the group consisting of anhydrides, imides, esters, carboxylic acids, amines, alcohols, thiols, and isocyanates.

If the dienophile is maleic anhydride, for example, then the C=C double bond contained therein corresponds to the dienophile unit, the anhydride group corresponds to the at least one further functional unit. Similar comments apply in respect of maleimide, for example. The C=C double bond therein corresponds to the dienophile unit, and the imide group corresponds to the at least one further functional unit.

Step ii) may be carried out at any temperature and at any pressure. Preferably step ii) is carried out at a temperature which is below the boiling point of the at least one solvent (LM) present in the dienophile-containing solution (dL) and/or below the melting temperature of the polyamide (P) present in the surface (O).

The temperature in step ii) is for example in the range from 15 to 150° C., preferably in the range from 20 to 100° C., and especially preferably in the range from 23 to 60° C.

The pressure in step ii) is situated for example in the range from 0.5 to 1.5 bar, preferably in the range from 0.8 to 1.2 bar, and especially preferably in the range from 0.9 to 1.1 bar.

The present invention accordingly also provides a process wherein step ii) is carried out at a temperature in the range from 15 to 150° C.

The surface-functionalized molding (oF) having the functionalized surface (fO) is preferably obtained by reacting the diene unit (I) of the polyamide (P) present in the surface (O) with the dienophile unit of the at least one dienophile present in the dienophile-containing solution (dL), in a [4+2] cycloaddition. [4+2] Cycloadditions are known per se to the skilled person. They are also referred to as Diels-Alder reactions.

In the [4+2] cycloaddition, the dienophile is added onto the furan unit (diene unit) by its dienophile unit that is reactive toward the furan units present in the polyamide (P), in other words preferably by the C=C double bond, the C=O double bond or the C=S double bond. As a result, a cyclohexene derivative is formed. This reaction is known per se to the skilled person.

The functionalized surface (fO) therefore comprises cyclohexene derivative units.

The skilled person is aware that the [4+2] cycloaddition is reversible. This reaction is referred to as a retro-Diels-Alder reaction. The temperatures at which the retro-Diels-Alder reaction takes place are dependent on the nature of the at least one dienophile. Step ii) is carried out preferably at a temperature which is below the temperature at which the retro-Diels-Alder reaction takes place.

In the reaction of the dienophile units of the at least one dienophile with the diene units (I) of the polyamide (P), each of the diene units (I) present in the polyamide (P) may react with in each case one dienophile unit. It is also possible for only a portion of the diene units (I) present in the polyamide (P) to react with the dienophile units of the at least one dienophile.

It is self-evident that the functionalized surface (fO) is formed at the locations at which the surface (O) of the molding (F) is brought into contact with the dienophile-containing solution (dL).

On the macroscopic scale, the shape of the molding (F) remains unchanged during the reaction of the dienophile units with the diene units (I). The surface-functionalized molding (oF) therefore has the same macroscopic shape as the molding (F). Macroscopically, therefore, the surface-functionalized molding (oF) is subject to the same observations and preferences as described above for the molding (F), mutatis mutandis.

It is self-evident that as a result of the reaction of the polyamide (P) present in the surface (O), the surface (O) is modified to give the functionalized surface (fO). At a molecular level, therefore, the shape of the molding will be changed. On formation of the functionalized surface (fO), the thickness of the surface (O) increases by the length of the dienophile molecules and also, optionally, the length of the molecules of the functionalizing agent (FM). The functionalized surface (fO) therefore has a greater thickness than the unfunctionalized surface (the surface (O)).

In one embodiment of the invention the following step is carried out subsequent to step ii).

iii) contacting the functionalized surface (fO) of the surface-functionalized molding (oF) obtained in step ii) with at least one functionalizing agent (FM) which comprises at least one reactive unit which is reactive toward the at least one further functional unit present in the at least one dienophile.

The present invention accordingly also provides a process wherein the step below is carried out subsequent to step ii):

iii) contacting the functionalized surface (fO) of the surface-functionalized molding (oF) obtained in step ii) with at least one functionalizing agent (FM) which comprises at least one reactive unit which is reactive toward the at least one further functional unit present in the at least one dienophile.

The contacting of the functionalized surface (fO) of the surface-functionalized molding (oF) obtained in step ii) with the at least one functionalizing agent (FM) may take place by any methods known to the skilled person. Contacting may take place, for example, by the functionalized surface (fO) being immersed into the functionalizing agent (FM) or by the functionalizing agent (FM) being applied to the functionalized surface (fO) by spraying, rolling, knife coating or brushing. Techniques of doing this are known to the skilled person. Preferably the functionalized surface (fO) is brought into contact with the functionalizing agent (FM) by the functionalized surface (fO) being immersed into the functionalizing agent (FM).

The at least one functionalizing agent (FM) may be used as such. It is also possible for a solution of the at least one functionalizing agent (FM) to be used. Suitable solvents are those known to the skilled person and are preferably solvents in which the functionalized surface (fO) is insoluble and the at least one functionalizing agent (FM) is soluble.

Suitable solvents are selected for example from the group consisting of acetone, acetonitrile, N-methyl-2-pyrrolidone, dimethylformamide, dimethyl sulfoxide, hexane, toluene, diethyl ether, tetrahydrofuran, methylene chloride, chloroform, 1,2-dichlorobenzene, water, methanol, ethanol, isopropanol, and mixtures thereof.

If a solution of the at least one functionalizing agent (FM) is used, the solution comprises for example in the range from 0 to 99.5 wt % of the solvent and in the range from 0.5 to 100 wt % of the functionalizing agent (FM), preferably in the range from 70 to 98 wt % of the solvents and in the range from 2 to 30 wt % of the functionalizing agent (FM), based in each case on the sum of the weight percentages of the solvent and of the functionalizing agent (FM), preferably based on the total weight of the solution.

The at least one functionalizing agent (FM) comprises at least one reactive unit which is reactive toward the at least one further functional unit present in the at least one dienophile.

It is self-evident that the at least one functionalizing agent (FM) is different from the at least one dienophile.

The at least one reactive unit present in the at least one functionalizing agent (FM) is preferably selected from the group consisting of amines, alcoholen, thiols, isocyanates, carboxylic acids, and anhydrides.

The present invention accordingly also provides a process wherein the at least one reactive unit present in the at least one functionalizing agent (FM) is selected from the group consisting of amines, alcohols, thiols, isocyanates, carboxylic acids, and anhydrides.

When the functionalized surface (fO) of the surface-functionalized molding (oF) obtained in step ii) is brought into contact with the at least one functionalizing agent (FM), the at least one reactive unit which is present in the functionalizing agent (FM) enters into a reaction with the at least one further functional unit present in the dienophile. In this procedure the functionalized surface (fO) is further functionalized. These reactions are known per se to the skilled person. Where, for example, the dienophile comprises an anhydride group as further functional unit and the functionalizing agent (FM) comprises an amine as reactive unit, the reaction of the further functional unit with the reactive unit forms an amide. This amide is then able at higher temperatures to undergo reaction to form an imide. This reaction is known to the skilled person.

The present invention further provides a surface-functionalized molding (oF) obtainable by the process of the invention.

The present invention is illustrated hereinafter by examples, without being restricted thereto.

EXAMPLES

For the measurement of the contact angle, the powders obtained were applied to a flat glass surface and the contact angle of water drops on the powders was determined using a Krüss DA 100. For this purpose, using double-sided adhesive tape, a powder layer was produced on a glass slide. For the determination of the contact angle, drops of deionized water of about 2 µl in size were placed onto the powder layer and subjected to measurement at 23° C.

Comparative Example 1

Pellets of PA6/F6 (80/20) (W/W), copolymer of caprolactam (80 wt %) with 2,5-bis(aminomethyl)furan and adipic acid (together 20 wt %), were ground under liquid nitrogen in a Retsch ZM 200 cryomill and then sieved to give a powder having a particle size of <500 µm. The powder was dried in a vacuum oven at 80° C. The contact angle was 112.9°.

Example 2

5 g of the powder from comparative example 1 were suspended for 24 hours in a 0.1-molar solution of 1,1'-(methylenedi-4,1-phenylene)bismaleimide solution in toluene (dienophile-containing solution (dL)) and stirred therein. Subsequently the powder was filtered, washed five times with toluene, and filtered. The powder was subsequently dried in a vacuum oven at 80° C. for 24 hours. The contact angle was 103.8°.

Example 3

10 g of the powder from comparative example 1 were suspended for 24 hours in a 1-molar solution of maleic anhydride solution in toluene (dienophile-containing solution (dL)) and stirred therein. Subsequently the powder was filtered, washed five times with toluene, and filtered. The powder was subsequently dried in a vacuum oven at 80° C. for 24 hours.

Example 4

5 g of the powder obtained in example 3 were suspended in a 1-molar solution of 1-octadecylamine in toluene (solution of the functionalizing agent (FM)) and then stirred for 24 hours. The powder obtained was filtered, washed five times with toluene, and filtered again. The powder obtained was then dried under reduced pressure at 80° C. for 24 hours. The contact angle was 123.6°.

Example 5

5 g of the powder obtained in example 3 were suspended in water for 24 hours and stirred therein. Subsequently the powder was filtered and then dried in a vacuum oven at 80° C. for 48 hours. The contact angle was 71.2°.

From the comparison of the contact angles for the various powders obtained in the examples it is clearly apparent that the surface of PA6/F6 can be modified hydrophobically or hydrophilically by the reaction with a dienophile. When the PA6/F6 powder is treated with maleic anhydride and the product obtained is subsequently reacted with 1-aminooctadecane (example 4), the contact angle is increased significantly, indicating that the surface becomes more hydrophobic. In contrast, on reaction of the polyamide powder with maleic anhydride and subsequently water, the contact angle is significantly lowered, pointing to a greater hydrophilicity on the part of the polyamide.

The invention claimed is:

1. A process for producing a surface-functionalized molding (oF) having a functionalized surface (fO), comprising the steps of
    i) providing a molding (F) having a surface (O) which comprises a polyamide (P), the polyamide (P) comprising diene units of the general formula (I)

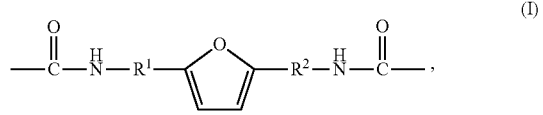

(I)

in which
R$^1$ and R$^2$ independently of one another are selected from C$_1$-C$_{10}$ alkanediyl,
    ii) contacting the surface (O) of the molding (F) provided in step i) with a dienophile-containing solution (dL) which comprises at least one dienophile, the at least one dienophile comprising at least one dienophile unit which is reactive toward the diene units (I) present in the polyamide (P), to give the surface-functionalized molding (oF) having the functionalized surface (fO).

2. The process according to claim 1, wherein in step ii) the at least one dienophile unit present in the at least one dienophile reacts with the diene units (I) present in polyamide (P) in a [4+2] cycloaddition to give the surface-functionalized molding (oF).

3. The process according to claim 1, wherein the dienophile-containing solution (dL) comprises at least one solvent (LM).

4. The process according to claim 3, wherein the at least one solvent (LM) is selected from the group consisting of acetone, acetonitrile, N-methyl-2-pyrrolidone, dimethylformamide, dimethyl sulfoxide, hexane, toluene, diethyl ether, tetrahydrofuran, methylene chloride, chloroform, 1,2-dichlorobenzene, water, methanol, ethanol, and isopropanol.

5. The process according to claim 3, wherein the dienophile-containing solution (dL) comprises in the range from 0 to 99.5 wt % of the at least one solvent (LM) and in the range from 0.5 to 100 wt % of the at least one dienophile, based in each case on the total weight of the dienophile-containing solution (dL).

6. The process according to claim 1, wherein the at least one dienophile unit present in the at least one dienophile is selected from the group consisting of C=C double bonds, C=O double bonds, and C=S double bonds.

7. The process according to claim 1, wherein the at least one dienophile present in the dienophile-containing solution (dL) comprises at least one structural unit selected from the group consisting of maleimides, benzophenone, acrylates, methacrylates, acrylonitriles, maleic acid, maleic anhydride, and maleic esters.

8. The process according to claim 1, wherein the at least one dienophile present in the dienophile-containing solution (dL) comprises exactly one dienophile unit.

9. The process according to claim 1, wherein step ii) is carried out at a temperature in the range from 15 to 150° C.

10. The process according to claim 1, wherein the at least one dienophile present in the dienophile-containing solution (dL) comprises at least one further functional unit.

11. The process according to claim 10, wherein the at least one further functional unit is selected from the group consisting of anhydrides, imides, esters, carboxylic acids, amines, alcohols, thiols, and isocyanates.

12. The process according to claim 10, wherein the following step is carried out subsequent to step ii):
    iii) contacting the functionalized surface (fO) of the surface-functionalized molding (oF) obtained in step ii) with at least one functionalizing agent (FM) which comprises at least one reactive unit which is reactive toward the at least one further functional unit present in the at least one dienophile.

13. The process according to claim 12, wherein the at least one reactive unit present in the at least one functionalizing agent (FM) is selected from the group consisting of amines, alcohols, thiols, isocyanates, carboxylic acids, and anhydrides.

14. A surface-functionalized molding (oF) obtainable by the process according to claim 1.

* * * * *

UNITED STATES PATENT AND TRADEMARK OFFICE
CERTIFICATE OF CORRECTION

PATENT NO. : 10,245,617 B2
APPLICATION NO. : 15/741300
DATED : April 2, 2019
INVENTOR(S) : Gijsbrecht Jacobus Maria Habraken et al.

It is certified that error appears in the above-identified patent and that said Letters Patent is hereby corrected as shown below:

In the Claims

At Column 17, Line 43, Claim 1 "(0)" should be -- (O) --.

Signed and Sealed this
Twenty-fourth Day of September, 2019

Andrei Iancu
*Director of the United States Patent and Trademark Office*